United States Patent [19]

Kendall-Tobias

[11] Patent Number: 4,571,172
[45] Date of Patent: Feb. 18, 1986

[54] SYSTEM FOR CHANGING OXIDANTS IN A FLAME ATOMIC ABSORPTION SPECTROPHOTOMETER

[75] Inventor: Michael W. Kendall-Tobias, Danbury, Conn.

[73] Assignee: The Perkin-Elmer Corporation, Norwalk, Conn.

[21] Appl. No.: 670,713

[22] Filed: Nov. 13, 1984

[51] Int. Cl.[4] ............................................. G01J 3/30
[52] U.S. Cl. ...................................... 431/62; 431/90; 356/315; 356/417
[58] Field of Search ................ 356/315, 417; 431/90, 431/6, 62

[56] References Cited

U.S. PATENT DOCUMENTS 4,250,553  2/1981  Sebens et al. ........................ 356/315
4,314,764  2/1982  Liddell et al. ........................ 356/315

Primary Examiner—Carroll B. Dority, Jr.
Attorney, Agent, or Firm—E. T. Grimes; F. L. Masselle

[57] ABSTRACT

A flame atomic absorption spectrophotometer burner apparatus for burning a fuel such as acetylene as one essential gas in the oxidant such as nitrous oxide as another essential gas includes a system for safely changing oxidants between air and nitrous oxide during start up. The system has a pressure sensor for sensing the pressure of at least one of the essential gasses, and a valve selectively operable in response to the pressure sensor for effecting the supplying of air as the oxidant and continuing to supply air as the oxidant when the pressure of the essential gas is low and for selectively switching to nitrous oxide as the oxidant only when the pressure of the essential gas is high.

13 Claims, 1 Drawing Figure

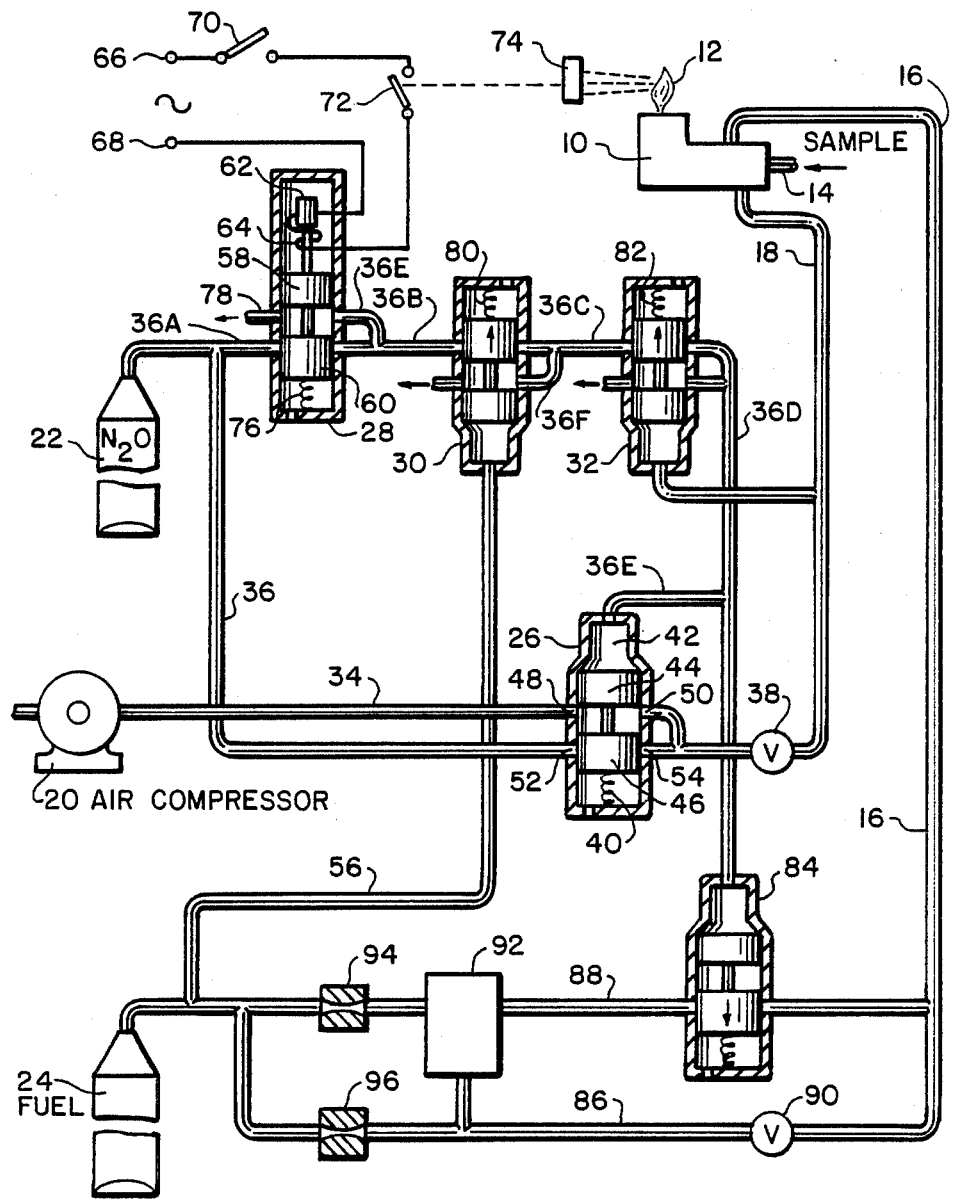

SYSTEM FOR CHANGING OXIDANTS IN A FLAME ATOMIC ABSORPTION SPECTROPHOTOMETER

BACKGROUND OF THE INVENTION

The present invention relates to a flame atomic absorption spectrophotometer of the type which requires air as a start-up and shut-down oxidant and uses nitrous oxide as a high energy oxidant for the burner flame. The present invention particularly relates to an improved apparatus for safely changing from air as the oxidant to nitrous oxide as the oxidant, and back again.

In atomic absorption spectroscopy, the measurement of the absorption of a radiation beam at a characteristic resonant spectral line for a particular element yields a measure of the concentration of that element in an original sample solution. Presently, one of the most common techniques for atomizing an element for purposes of the absorption measurement is by introducing a liquid sample solution of the element of interest into a gas burner wherein droplets of the solution are vaporized and the elements ultimately atomized, so as to form in the path of the apparatus radiation beam, a substantial quantity of the element of interest in its atomic state. A sample light beam, which originates from a line-emitting light source, and which includes a resonance line of the element to be measured, is directed through the flame. The desired element in the sample absorbs the resonance lines characteristic of the element and the emerging light beam is directed to a monochromator and thence to a detector which measures the degree to which the desired element absorbs the resonance lines of the sample beam. This absorption degree represents the amount of desired element in the sample substance.

In such spectrophotometers, in order to produce a flame which has a high enough temperature for the best measurement results for certain elements, it is preferred to use acetylene gas as a fuel and to use nitrous oxide ($N_2O$) as the source of oxygen for the combustion of the acetylene gas. In order to initiate combustion in a safe manner, it is necessary to begin combustion of the acetylene gas using air as the oxygen source, and to then switch over to the nitrous oxide after the acetylene gas flame is ignited and stable.

The essential gases for the steady-state high temperature operation of the burner of a flame atomic absorption spectrophotometer, as described above, are the fuel acetylene and the oxidant nitrous oxide. It is important that both of these essential gases be available in adequate quantities for the system to successfully shift from operation on air to operation on nitrous oxide during start-up, and that those essential gases continue in adequate supply in order to sustain operation on nitrous oxide.

It is also important that there must be a flame at the time of switch-over from air to nitrous oxide, and that the flame be maintained in order to support operation on nitrous oxide. Furthermore, since the entire control system of the spectrophotometer is usually operated by electrical power, including the control of fuel flow, it is important that electric power should continue to be available during operation under nitrous oxide. Still further, it is important that a sufficient volume of oxidant, under sufficient pressure, should be available at the burner of the flame atomic absorption spectrophotometer (not having been reduced too much by the manual flow control adjustment valve) in order to provide for a successful change-over from air to nitrous oxide.

In prior burner control systems, the operator has been relied upon for assuring that some or all of the above mentioned conditions were met in switching from air as the start up oxidant to nitrous oxide as the running oxidant and for assuring that the conditions are maintained. Such an arrangement involves risks because of possible operator error or inattention, and the result can often be an explosion, or improper combustion. Furthermore, some of the above conditions are not immediately apparent to the operator.

Accordingly, it is an important object of the present invention to provide an improved burner control system for a flame atomic absorption spectrophotometer apparatus in which one or more of the above listed requirements for safe switching from air to nitrous oxide as the oxidant are automatically assured, and in which the switch over to nitrous oxide cannot be made without the fulfillment of the condition or conditions.

One prior arrangement for inexpensive burner systems involves the use of a separate valve for each oxidant source, the change over being accomplished by simply closing the valve for one oxidant while opening the valve for the other oxidant. Such a procedure involves the risk that the change over may be slow, resulting in undesirable fuel-oxidant mixtures, or that the oxidant from one source may be completely shut off before the oxidant from the other source is turned on. This may result in extinguishment of the flame together with the risk of possible later explosion if the change is being made to nitrous oxide.

Another object of the invention is to provide an improved burner system which includes an improved means for switching over from one oxidant to the other in a very rapid manner so as to avoid the possibility of improper fuel-oxidant mixtures.

Another object of the invention is to provide an improved burner system for a flame atomic absorption spectrophotometer which is operable to switch from one oxidant to another while avoiding any risk of an interval with both oxidants shut off.

It is another object of the invention to provide an improved burner system for a flame atomic absorption spectrophotometer apparatus which automatically fulfills one or more of the above mentioned requirements for safe operation and which is very efficient and cost effective.

Other objects and advantages of the invention will be apparent from the following description and the accompanying drawings.

SUMMARY OF THE INVENTION

In carrying out the invention there is provided a flame atomic absorption spectrophotometer burner apparatus for burning a fuel such as acetylene as one essential gas in an oxidant such as nitrous oxide as another essential gas, a system for safely changing oxidants between air and nitrous oxide during start up comprising means for sensing the pressure of at least one of said essential gasses, and means selectively operable in response to said pressure sensing means for effecting the supplying of air as the oxidant and continuing to supply air as the oxidant when the pressure of said essential gas is low and for selectively switching to nitrous oxide as the oxidant only when the essential gas pressure is high.

BRIEF DESCRIPTION OF THE DRAWINGS

The drawing is a schematic diagram of a burner system in accordance with a preferred embodiment of the present invention.

DETAILED DESCRIPTION

Referring more particularly to the drawing, the burner for a flame atomic absorption spectrophotometer is schematically shown at 10, which normally has a flame 12 when in operation. The burner contains a nebulizer into which a liquid sample for analysis is introduced through an inlet 14. Acetylene fuel is supplied to the burner through a conduit 16, and oxidant through a conduit 18.

The oxidant for conduit 18 is supplied either as air from a compressed air source such as air compressor 20, or as nitrous oxide from a source such as a pressure canister schematically indicated at 22. The fuel for the fuel line 16 is supplied from a fuel source such as a canister indicated at 24.

The nitrous oxide from canister 22 and the fuel from canister 24 are sometimes referred to in this specification as "essential" gases because they are both essential for maintaining a flame in the selected mode, different from the default mode of operation which involves an air and acetylene mixture.

Briefly and broadly described, the system includes a pressure actuated switching valve 26 which is controlled by one or more pilot valves 28, 30, and 32. The switching valve 26 is operable to switch the supply of oxidant from the air compressor 20 through an air conduit 34 to the nitrous oxide supplied from canister 22 through a conduit 36. A manual control valve 38 is provided in the oxidant line to adjust the flow of either oxidant to the burner 10.

Assuming all of the pilot valves 28, 30, and 32 are open, the switching valve 26 receives actuating pressure through the sensing line conduit sections 36A, 36B, 36C, 36D, and 36E from the nitrous oxide source 22. The switching valve 26 is preferably spring biased, as schematically illustrated by a spring 40, with a spring force which is overcome by nitrous oxide pressure in the chamber 42 when that pressure is at, or above, an adequate nitrous oxide operating pressure for the system. Thus, the switching valve itself senses the adequacy of the nitrous oxide pressure, and thus measures the adequacy of the nitrous oxide supply as a condition of operation.

All of the valves are shown in a simplified schematic section form to illustrate the principle of operation of each valve in the system. It will be understood that the valves may be constructed in various ways and may incorporate various refinements which are not illustrated.

The switching valve 26 is illustrated as including two valve lands 44 and 46. The valve is shown in the "air" position as biased by the spring 40 in the absence of substantial pressure in pressure chamber 42. In this position, the air ports 48 and 50 are open to provide for delivery of air as the oxidant. Upon the presence of sufficient nitrous oxide pressure in chamber 42, the valve piston moves downwardly and the ports 48 and 50 are closed by land 44. Substantially concurrently, land 46 opens up ports 52 and 54 to provide for delivery of nitrous oxide instead of air through the conduit 36.

The valve 26 may be characterized as a means for sensing the available pressure of at least one of the essential gases (nitrous oxide). The valve 26 may also be characterized as a means selectively operable in response to the sensing of the available pressure of the essential gas for effecting the supplying of air as the oxidant and continuing to supply air as the oxidant when the pressure of the essential gas is low and for selectively switching to nitrous oxide as the oxidant only when the essential gas pressure is high. The biasing spring 40 is operable to switch off the nitrous oxide, and to switch on the air if the nitrous oxide supply is depleted sufficiently to cause the pressure to drop below the bias force as sensed in the switching valve 26.

Pilot valve 32 is a pressure actuated valve which responds to the oxidant pressure in conduit 18 as supplied to the burner 10. The pilot valve 30 is a pressure actuated valve which responds to the pressure of the fuel supply from canister 24 through a conduit 56.

The pilot valve 28 is a solenoid actuated pilot valve with a piston having lands 58 and 60 which is movable by means of a solenoid 20 plunger 62 under the electromagnetic force from a winding 64. The structure is illustrated in an idealized schematic form. The winding 64 is energized from the main power source as indicated by the terminals 66 and 68 through 25 switches 70 and 72. Switch 70 is closed manually when nitrous oxide operation is to be initiated by the operator. Switch 72 is a schematic representation of a switch (or relay contact) which is actuated by a flame sensing device such as a photo cell 74 in response to illumination from the flame 12. Thus, the switch 72 is closed if the flame is present, and open if the flame is absent.

Therefore, if there is no flame, the solenoid valve 28 is not actuated, and the system cannot be shifted over to nitrous oxide operation even if the manual switch 70 is closed. Furthermore, if the flame goes out, the flame sensor 74 control of switch 72 releases the solenoid valve so that it closes under the force of a biasing spring 76, which causes the system to switch back to air as the oxidant. When the solenoid is not energized, the piston of the solenoid valve is biased closed by spring 76 as shown, with the piston land 60 closing the ports associated with conduits 36A and 36B. At the same time, conduit 36B is vented through a branch conduit 36E and an exhaust port 78. When the solenoid is energized, piston land 60 moves downwardly, uncovering the ports associated with conduits 36A and 36B so as to provide an interconnection between the two, and piston land 58 covers the ports at conduit branch 36E and 78 to close off that exhaust path.

Whenever the solenoid is de-energized, such as by the loss of the flame, the piston returns to the raised position illustrated in the drawing, closing off the ports associated with conduits 36A and 36B, and opening the exhaust path to assure the immediate reduction of pressure in conduit 36B so as to cause the switching valve 26 to immediately switch the system back to air as the oxidant.

It will be apparent that the system is also automatically switched back to air as the oxidant if system power fails, or is shut off, or if the selector switch 70 is opened to de-energize the solenoid The pressure actuated pilot valve 30 includes a biasing spring 80 which provides an appropriate bias to determine the minimum fuel pressure at which conversion to operation with nitrous oxide as the oxidant is to be permitted. Whenever that pressure is equalled or exceeded, the piston of that pilot valve is forced 15 upwardly, opening the ports associated with the conduits 36B and 36C to transmit the control pressure through to the switching valve 26. At the same time, the lower land of the valve piston closes off an exhaust which otherwise exhausts the pressure in conduit 36C through a branch 36F.

The pressure actuated pilot valve 32 may be substantially identical to the pilot valve 30, and operates in a similar manner, except that the biasing spring 82 will typically have a different spring constant in order to set a different minimum pressure for the oxidant output supply which permits the switching to nitrous oxide.

In accordance with another preferred feature of the invention, a second switching valve 84 is provided for increasing the flow of fuel through the fuel conduit 16 when the oxidant supply is switched from air to nitrous oxide. The switching valve 84 is substantially identical to the switching valve 26, except for the omission of ports 48 and 50. The spring bias of switching valve 84 is selected to be slightly less than the spring bias of spring 40 of switching valve 26 so that the fuel switching valve 84 will be sure to operate whenever the switching valve 26 operates so that there will always be an additional acetylene supply whenever nitrous oxide is switched in as the oxidant.

As shown in the drawing, the fuel supply system includes two parallel paths, a master path represented by conduit 86, and a slave path represented by conduit 88. When operation is carried out with air as the oxidant, fuel is supplied only through the master path 86, which includes a manual fuel flow adjusting valve 90. When the slave path 88 is opened by the switching valve 84, the flow through the slave path 88 is controlled to be proportional to, and preferably substantially equal to the flow through the master path 86. This is accomplished by means of a pressure responsive flow control valve 92 which detects and responds to the respective flows in the master and slave paths by the detection of pressure drops through orifice devices 94 and 96. This fluid flow control apparatus, including the valve 92, and the orifices 94 and 96, forms at least a part of the subject matter of a co-pending patent application Ser. No. 670,714 filed concurrently with the present application for a FLUID FLOW CONTROL SYSTEM and assigned to the same assignee as the present invention.

While the switching valve 26 (and the switching valve 84) are shown as controlled by a combination of three separate series connected pilot valves 28, 30, and 32. It will be appreciated that if all of the recited control functions are not desired, only one or two of these pilot valves may be employed. When the pressure sensing conduit line 36A-36E is pressurized by the operation of all of the pilot valves the switch over from air to nitrous oxide is rapidly accomplished, while avoiding any risk that both oxidants are shut off at any time. While not necessarily evident from the drawing, the spacing of the lands 44 and 46 in valve 26 is preferably such that as the ports 48 and 50 for the air are cut off, the ports 52 and 54 are being opened up.

While the switching valves 26 and 84 are illustrated in the drawing as substantially the same size as the pilot valves 28, 30, and 32, it will be understood that, since the pilot valves need not provide for a substantial fluid flow, and are only basically pressure gating devices, the pilot valves may be much smaller than the switching valves 26 and 84. Thus, much less expensive structures are required for the pilot valves. This is an important economic advantage in the present invention. Thus, for instance, if a solenoid valve is employed in place of the switching valve 26, a much larger, and more expensive solenoid valve is required. Also, a large switching valve 26 which is simply pressure actuated, as in the present system, is considerably less expensive than a solenoid valve of the same capacity. Accordingly, there is an over-all saving in the combination of the solenoid valve 28 and the switching valve 26, in addition to the attributes of response to various conditions, including a minimum nitrous oxide pressure.

As previously mentioned, the switching valves 26 and 84, and the pilot valves 28, 30, and 32, are illustrated schematically to promote the understanding of the system. It will be understood that various pneumatic valve structures may be used which accomplish the same functions. Such valve structures are commercially available from vendors such as Clippard Instrument Laboratory, Inc., 7390 Colerain Road, Cincinnati, Ohio 45239.

While this invention has been shown and described in connection with particular preferred embodiments, various alterations and modifications will occur to those skilled in the art. Accordingly, the following claims are intended to define the valid scope of this invention over the prior art, and to cover all changes and modifications falling within the true spirit and valid scope of this invention.

What is claimed is:

1. In a flame atomic absorption spectrophotometer burner apparatus for burning a fuel such as acetylene as one essential gas in an oxidant such as nitrous oxide as another essential gas, a system for safely changing oxidants between air and nitrous oxide during start up comprising means for sensing the pressure of at least one of said essential gasses, and means selectively operable in response to said pressure sensing means for effecting the supplying of air as the oxidant and continuing to supply air as the oxidant when the pressure of said essential gas is low and for selectively switching to nitrous oxide as the oxidant only when the essential gas pressure is high.

2. Apparatus as claimed in claim 1 wherein nitrous oxide is the essential gas for which the available pressure is sensed by said pressure sensing means.

3. An apparatus in accordance with claim 2 wherein said means for sensing the pressure of the available nitrous oxide and said means for switching to nitrous oxide as the oxidant when the pressure is high are combined in a pressure operated switching valve which is operable to switch from air to nitrous oxide in response to a sufficiently high nitrous oxide pressure, said valve including a biasing means for biasing the valve to switch on air and to switch off nitrous oxide against the force of the sensed nitrous oxide pressure.

4. Apparatus as claimed in claim 3 wherein a pressure sensing line is connected to said switching valve, at least one pilot valve connected in said pressure sensing line and operable to connect nitrous oxide from a nitrous oxide source through said sensing line to said switching valve to effectuate the switching thereof.

5. Apparatus as claimed in claim 4 wherein said pilot valve is solenoid actuated and includes an actuating solenoid, a solenoid actuating circuit including a switch means for controlling said solenoid to open said pilot valve to select operation with nitrous oxide as the oxidant, said solenoid circuit being connected and arranged to receive power from the power source which supplies other electrical components of the flame atomic absorption spectrophotometer so that said solenoid is de-energized upon system power failure to thereby close the pilot valve and cause said switching valve to switch the burner system back to operation on air as the oxidant.

6. Apparatus as claimed in claim 5 including a flame detector for detecting the presence of a flame in the burner of the flame atomic absorption spectrophotometer, switching means connected for actuation in response to said flame detector and connected in said solenoid actuating circuit, said last named switching means being operable to close the solenoid circuit in response to the presence of a flame and to open in the absence of a flame to prevent operation of said solenoid actuated pilot valve and switching of the burner system to nitrous oxide as an oxidant in the absence of a flame.

7. Apparatus as claimed in claim 4 wherein a means is provided for detecting the presence of a flame in the burner of the flame atomic absorption spectrophotometer, said last named means being connected to said pilot valve and being operable to provide for operation of said pilot valve to switch the operation of the burner to nitrous oxide only in the presence of a flame at the burner.

8. Apparatus as claimed in claim 4 wherein there is provided a conduit downstream from said switching valve for conveying oxidant to the burner, a control valve in said conduit for controlling the rate of flow of oxidant to the burner, said pilot valve being a gas pressure operated pilot valve, an operating pressure connection from said pilot valve to said oxidant conduit downstream from said control valve for detecting the presence of at least a minimum pressure of oxidant supplied to said burner and operable only upon the achievement of said minimum pressure to connect nitrous oxide pressure through said sensing line to said switching valve to switch the burner system from air to nitrous oxide.

9. Apparatus as claimed in claim 4 wherein said pilot valve is a gas pressure operated pilot valve, an operating pressure connection from said pilot valve for connection to a source of fuel for the burner and for detecting the presence of at least a minimum pressure of fuel to be supplied to said burner and operable only upon the achievement of said minimum pressure to connect nitrous oxide pressure through said sensing line to said switching valve to switch the burner system from air to nitrous oxide.

10. Apparatus as claimed in claim 4 including a fuel supply system for supplying fuel to the burner of the flame atomic absorption spectrophotometer, said fuel system including a master fuel path and a slave fuel path, the slave fuel path being arranged to be opened up to supply additional fuel when the system is switched over to operate with nitrous oxide oxidant, the system also including a second switching valve connected in said slave fuel conduit, said second switching valve being connected in said pressure sensing line and being operable to open in response to the nitrous oxide pressure in said sensing line substantially concurrently with the opening of said first mentioned switching valve so that an additional supply of fuel is available at the same time that the apparatus is switched over from air to nitrous oxide as the oxidant.

11. Apparatus as claimed in claim 5 wherein a second pilot valve is connected in series in said pressure sensing line, said second pilot valve being a gas pressure operated pilot valve, an operating pressure connection from said second pilot valve for connection to a source of fuel for the burner for detecting the presence of at least a minimum pressure of fuel to be supplied to said burner and operable only upon the achievement of said minimum pressure to connect nitrous oxide pressure to said switching valve to switch the burner system from air to nitrous oxide.

12. Apparatus as claimed in claim 11 wherein there is provided a third pilot valve connected in series with said first mentioned pilot valve and with said second pilot valve in said pressure sensing line, and wherein there is provided a conduit downstream from said switching valve for conveying oxidant to the burner, a control valve in said conduit for controlling the rate of flow of oxidant to the burner, said third pilot valve being a gas pressure operated pilot valve and including an operating pressure connection to said oxidant conduit downstream from said control valve for detecting the presence of at least a minimum pressure of oxidant supplied to said burner and operable only upon the achievement of said minimum pressure to connect nitrous oxide pressure through said sensing line to said switching valve to switch the burner system from air to nitrous oxide.

13. Apparatus as claimed in claim 12 including a fuel supply system for supplying fuel to the burner of the flame atomic absorption spectrophotometer, said fuel system including a master fuel path and a slave fuel path, the slave fuel path being arranged to be opened up to supply additional fuel when the system is switched over to operate with nitrous oxide oxidant, the system also including a second switching valve connected in said slave fuel conduit, said second switching valve being connected in said pressure sensing line and being operable to open in response to the nitrous oxide pressure in said sensing line substantially concurrently with the opening of said first mentioned switching valve so that an additional supply of fuel is available at the same time that the apparatus is switched over from air to nitrous oxide as the oxidant.

* * * * *